United States Patent [19]
Ushimaru et al.

[11] Patent Number: 5,368,861
[45] Date of Patent: Nov. 29, 1994

[54] GASTRIC PREPARATION WITH SUSTAINED RELEASE

[75] Inventors: Kouichi Ushimaru, Kyoto; Kouichi Nakamichi, Shiga; Hiroyuki Yasuura, Shige, all of Japan

[73] Assignee: Nippon Shinyaku Co., Ltd., Japan

[21] Appl. No.: 852,130

[22] PCT Filed: Oct. 24, 1990

[86] PCT No.: PCT/JP90/01365
§ 371 Date: Apr. 24, 1992
§ 102(e) Date: Apr. 24, 1992

[87] PCT Pub. No.: WO91/06281
PCT Pub. Date: May 16, 1991

[30] Foreign Application Priority Data
Oct. 26, 1989 [JP] Japan .................. 1-279293

[51] Int. Cl.$^5$ .................. A61K 9/52; A61K 47/00
[52] U.S. Cl. .................. 424/451; 424/452; 424/457; 424/472; 424/458; 514/772.2; 514/772.3; 514/773; 514/777; 514/778; 514/781; 514/786; 514/783
[58] Field of Search .............. 424/457, 453, 472, 451, 424/454, 502

[56] References Cited

U.S. PATENT DOCUMENTS

| | | | |
|---|---|---|---|
| 2,951,792 | 9/1960 | Swintosky | 424/472 |
| 4,424,235 | 1/1984 | Sheth et al. | 424/319 |
| 4,702,918 | 10/1987 | Ushimaru et al. | 424/461 |
| 4,888,178 | 12/1989 | Rotini et al. | 424/468 |
| 5,043,167 | 8/1991 | Rotini et al. | 424/490 |

FOREIGN PATENT DOCUMENTS

| | | |
|---|---|---|
| 58-26816 | 8/1981 | Japan . |
| 61-43108 | 8/1984 | Japan . |
| 2103486 | 8/1982 | United Kingdom . |

*Primary Examiner*—Thurman K. Page
*Assistant Examiner*—James M. Spear
*Attorney, Agent, or Firm*—Rosenman & Colin

[57] ABSTRACT

A gastric preparation developed in order to solve the technical problems of conventional preparations, which is prepared by the bilayer packing technique and comprises 5 to 60%, desirably 10 to 40% of a rapid release portion which can establish the therapeutic level of a drug shortly after the administration and 95 to 40%, desirably 90 to 60% of a sustained release portion which has a specific gravity or 1 or less and can maintain a satisfactory release rate.

10 Claims, 2 Drawing Sheets

GASTRIC PREPARATION WITH SUSTAINED RELEASE

FIELD OF THE INVENTION

The present invention relates to quite a novel preparation having the properties of rapidly releasing a drug in the digestive tract and at the same time, retaining the drug in the digestive tract for release gradually and optionally.

BACKGROUND OF THE INVENTION

Preparations having a sustained release property are clinically advantageous in many points in that the time of administration of a drug can be reduced to afford convenience to the patient, the effective concentration of a drug is maintained over a long period of time thereby to effectively keep its pharmaceutical effect, a definite concentration is maintained thereby to reduce toxicity and prevent development of side effects, and the like. In addition, release of a drug in the upper part of the digestive tract is expected for a drug which is desired to directly act in the stomach and in small intestine in the upper part thereof, or for a drug having absorption limited to the upper part of the small intestine. For such a drug, a medical preparation with sustained gastric release has been proposed.

As a technique for preparations with sustained gastric release, there is known a method utilizing selective action at the pylorus by administering, for example, a tablet or capsule having a large diameter (Ogata et al., Pharmaceutical Factory, 3 (9), page 477, 1983). According to this method, however, there are big differences between individuals. Furthermore, residence time may vary depending upon gastric conditions and its contents so that reliability is poor as the form of administering a drug. In addition, the size of the preparation increases difficulty in administration.

As another method, a preparation utilizing hydrophilic colloid (Japanese Patent Application Laid-Open No. 57315/83), a preparation obtained by molding in a hollow shape and coating an active substance on the outer layer (Japanese Patent Application Laid-Open No. 12411/80), a method using foamable microcapsules (Japanese Patent Application Laid-Open No. 76418/77) has been proposed. However, this method is complex and requires extremely severe conditions for production and requires many steps, which are disadvantageous in economical consideration and poorly practicable. In addition, these methods also involve defects that preparations are destroyed by gastric peristaltic motion thereby to lose suspendability and lose the sustained property.

In order to solve the problems described above, there is disclosed a method for producing a medical preparation which is simple and hence highly practical and can retain a drug in the stomach over a long period of time and can release a drug in a constant amount (Japanese Patent Application Laid-Open No. 43108/86). According to this method, a substance capable of forming gel in water, oils and fats which are solid at ambient temperature and a drug are mixed with each other, the mixture is heated to a temperature higher than the melting point of the oils and fats and then cooled to obtain the thus treated product. The product obtained by the method envelops therein many fine closed pores, thereby showing an apparent density of 1 or less. The product has a strength that can sufficiently stand gastric peristaltic motion and by doing so, retains the property of gradually releasing a drug while retaining the drug in the stomach.

In this preparation, however, the entire system of the mixture comprising the gel component, oil and fat component and a drug is solidified by the heating and cooling operations. Therefore, where it is desired to increase the concentration of a drug to a therapeutical level in a short time after administration, rapid initial release of the drug cannot be expected. With respect to release control in the sustained release part, it is possible to control the release to a certain extent by changing a proportion of the gel component and the oil and fat component. However, an excellent prevention effect is exhibited with these components alone and hence, where the content of a drug is extremely small, for example, or where a sparingly soluble drug is used, the preparation might not provide a sufficient release rate corresponding to various properties of drugs.

DISCLOSURE OF THE INVENTION

An object of the present invention is to overcome the aforesaid technical defects and develop a more effective medical preparation.

The characteristic feature of the present invention lies in providing both a rapid release portion and a sustained release portion in a unitary preparation.

Hereinafter the medical preparation of the present invention and a method for production thereof are described in detail.

The rapid release portion in the present invention is to ensure a therapeutic level of a drug in a short period of time after administration, in which rapid release is made to exhibit its effect, even when the preparation is finally heated and cooled.

In general, for adding the rapid release portion, there is considered a method in which the rapid release portion is simply mixed with the sustained release portion processed for medical preparation, a method for encapsulating the rapid release portion into capsules, a method for molding a mixture, etc. The preparation of the present invention has both the rapid release portion which can rapidly release a drug and the sustained release portion which has suspendability and strength and can slowly release a drug, even after the preparation is subjected to a heat treatment. In such a general method for adding the rapid release portion, the rapid release portion and the sustained release portion are present together. Therefore, when a heat treatment is performed in such a state, the rapid release portion is also hardened at the same time; in this case, rapid release from the rapid release portion cannot be expected.

In the present invention, therefore, this problem has been solved by adopting a bilayer packing technique so as not to mix the rapid release portion and the sustained release portion with each other.

That is, the bilayer packing technique comprises packing the rapid release portion and the sustained release portion, respectively, by intermittent packing and forming a powder layer comprising a bilayered rapid release portion and a sustained release portion in a packed container. The resulting composition is subjected to a heat treatment after molding or packing in a gelatin capsule, or as it stands. The thus obtained preparation is a molded preparation in which only the sustained release portion is hard and the rapid release portion is present in a powdery state.

A proportion of the rapid release portion contained is in the range of 5% to 60%, preferably 10% to 40%, based on 40% to 90%, preferably 60% to 90% of the sustained release portion. Where the proportion of the rapid release portion is less than 5%, packing becomes uneven, or when heated after packing in a capsule or when heated after molding, the rapid release portion and the sustained release portion are present as admixture, whereby there is a danger that rapid release from the rapid release portion might be lost.

Where the proportion exceeds 60%, the volume of the sustained release portion decreases and as the result, suspendability might be reduced.

The construction of the sustained release portion in accordance with the present invention is an improvement of that already disclosed (Japanese Patent Application Laid-Open No. 43108/86). The present invention is to utilize this technique.

In the present invention, the rapid release portion can be constructed by a drug itself in accordance with the present invention, or the drug and excipients which can be incorporated as ordinary components for medical preparations.

The rapid release portion of the present invention occupies 5% to 60% of the sustained release portion. More preferably, the rapid release portion is 10% to 40%. With the proportion less than the lower limit, initial release is too small to maintain the concentration of a drug after release on a constant level. With the amount exceeding the upper limit, initial release is excessive so that a later concentration of the drug is incompatible.

The sustained release portion is comprised of:
(a) a substance capable of producing a gel in water,
(b) an oil or fat which is solid under ambient temperature conditions,
(c) a drug, and
(d) a substance for controlling release of the drug.

Thus in its most preferred embodiment, the present invention is directed to a gastric preparation comprising a rapid release portion and a sustained release portion present simultaneously in said preparation by formation of a layer wherein said rapid release portion comprises a drug or a drug and an excipient; and further, wherein said sustained release portion comprises (a), (b), (c) and (d) as described above, and whereby the specific gravity of the preparation is not more than 1.

As the substance (a) capable of forming gel in water which is used in the present invention, any substance can be chosen so long as it can form hydrated gel when put in water. There are, for example, cellulose derivatives, starch derivatives, dextran derivatives, polysaccharides, rubbers, polypeptides, proteins, acrylic acid derivatives, vinyl derivatives, etc.

In more detail, representative examples of these substances include the following compounds.

1. Cellulose derivatives
carboxymethyl cellulose, carboxyethyl cellulose, carboxypropyl cellulose, an alkali salt of carboxymethyl cellulose, an alkali salt of carboxyethyl cellulose, an alkali salt of carboxypropyl cellulose, methyl cellulose, hydroxypropyl cellulose, hydroxyethyl cellulose.
2. Starch derivatives
alpha starch, alpha amylostarch, gelatinated starch, carboxymethylated starch, carboxyethylated starch, phosphated starch, acid-treated starch, oxidized starch, dialdehyde starch, soluble starch, thin-boiling starch, dextrin.
3. Dextran derivatives
dextran, dextran sulfate, carboxylmethyldextran.
4. Polysaccharides
alginic acid, pectinic acid, arabic acid, an alkali salt of arabic acid.
5. Rubbers
gum arabic, tragacanth, carrageenan.
6. Polypeptides
polyglutamic acid, polyaspartic acid, polylysine, polyarginine.
7. Proteins
gelatin, collagen, casein, albumin, globulin, gluten.
8. Acrylic acid derivatives
polyacrylic acid, polymethacrylic acid, an alkali salt of polymethacrylic acid, a copolymer of polyacrylic acid and polymethacrylic acid.
9. Vinyl derivatives
polyvinylpyrrolidone, polyvinyl alcohol.

As for the oil or fat (b) which is solid under ambient temperature conditions and used in the present invention, any oil on fat may be used as long as it is solid at ambient temperature. There are, for example, higher fatty acids, higher fatty acid ester derivatives, higher alcohols, higher alcohol ester derivatives, etc. In more detail, representative examples of the oil on fat include the following compounds.

1. Higher fatty acids
lauric acid, tridecanoic acid, myristic acid, pentadecanoic acid, palmitic acid, margaric acid, stearic acid, nonadecanoic acid, arachic acid, behenic acid, lignoseric acid, serotic acid, montanic acid.
2. Higher fatty acid ester derivatives
esters such as glycerine, ethylene glycol, propylene glycol, sorbitol, polyethylene glycol, etc. of the fatty acids listed in 1. described above; glycerides of saturated fatty acids obtained from animal and plant, a mixture thereof and hardened oil and fat of the glycerides derived from these animal and plant; glycerides of unsaturated fatty acids such as oleic acid, linoleic acid, linolenic acid, lisinolic acid, etc. and a mixture thereof.
3. Higher alcohols
pentadecanol, hexadecanol (cetyl alcohol), hetadecanol (stearyl alcohol, nonadecanol, eicosanol, wool alcohol, cholesterol.
4. Higher alcohol ester derivatives
cholesteryl palmitate, palmitate of plant sterol.

As the substance (d) which controls release of a drug and is used in the present invention, any substance can be used so long as it is hydrophilic or swellable and when a mixture of (a) the substance capable of forming gel in water and (b) the oil and fat which are solid at ambient temperature is heated to a temperature higher than the melting point of the oil and fat, an apparent density of the resulting composition is less than 1.0. Representative examples of these subtances include the following compounds:

Fine crystalline cellulose, hydroxypropyl cellulose of low substitution degree, corn starch, mannitol, refined sugar, lactose.

As the drug (c) used in the present invention, any kind of drug can be used so long as, when a mixture of (a) the substance capable of forming gel in water, (b) the oil and fat which are solid at ambient temperature and (d) the substance which controls release of a drug is heated to a temperature higher than the melting point of the oil and fat, an apparent density of the resulting composition is less than 1.0. Representative examples of these subtances include the following compounds.

1. Antiinflammatory agents
   Indomethacin, Aspirin, Diclofenac sodium, Ketoprofen, Ibuprofen, Mefenamic acid, Dexamethasone, Dexamethasone sodium sulfate, Hydrocortisone, Prednisolone, Azulene.
2. Antiulcer agents
   Sulpiride, Cetraxate hydrochloride, Gefarnate.
3. Coronary dilators
   Nifedipine, Isosorbide dinitrate, Nitroglycerine, Diltiazem hydrochloride, Trapidil, Dipyridamole, Dilazep hydrochloride, methyl 2,6-dimethyl-4-(2-nitrophenyl)-5-(2-oxo-1,3,2-dioxaphosphorinan-2-yl)-1,4-dihydropyridine -3-carboxylate.
4. Peripheral vasodilators
   Ifenprodil tartarate, Cinepazide maleate, Cyclandelate, Cinnarizine, Pentoxyfylline.
5. Antibiotics
   Ampicillin, Amoxicillin, Cefalexin, Erythromycin ethyl succinate, Bacampicillin hydrochloride, Minocycline hydrochloride.
6. Urinary antiseptics
   Pipemidic acid, Nalidixic acid.
7. Antipyretics
   Aspirin, Phenacetin, Isopropylantipyrine, Acetaminophen, Benzydamine hydrochloride.
8. Antispasmodics
   Propantheline bromide, Atropine sulfate, Oxobium bromide, Timepidium bromide, Butylscopolamine bromide.
9. Antitussives, anti-asthmatic agents
   Theophylline, Aminophylline, Methylephedrine hydrochloride, Procatechol hydrochloride, Trimetoxynal hydrochloride, Codeine phosphate, Cromoglicate Sodium, Tranylast, Clofedanol, Dextromethorphan hydrobromic acid
10. Diuretics
    Furosemide, Acetazolamide.
11. Amyotonic agents
    Chlorphenesin carbamate, Triperizone hydrochloride, Eperizone hydrochloride.
12. Cerebrometabolism improving agents
    Hopatenic acid Calcium, Meclofenoxate hydrochloride
13. Minor tranquilizers
    Oxazolam, Diazepam, Clonazepam, Metazepam, Temazepam, Fludiazepam.
14. Major tranquilizers
    Sulpiride, Clocapramine hydrochloride, Zotepine.
15. β-Blockers
    Pindolol, Propranolol hydrochloride, Carteolol hydrochloride, Metoprolol tartarate, Labetalol hydrochloride.
16. Anti-arrhythmic agents
    Procainamide hydrochloride, Disopyramide, Ajimalin, Quinidine sulfate
17. Agent for the treatment of gout
    Allopurinol
18. Blood coagulation inhibitor
    Ticlopidine hydrochloride
19. Anti-epileptic agents
    Phenytoin, Valproate Sodium
20. Anti-histaminic agents
    Chlorpheniramine maleate, Clemastine fumarate, Mequitazine, Alimemazine tartarate, Cycloheptazine hydrochloride.
21. Anti-vomiting agents
    Difenidol hydrochloride, Metoclopramide, Domperidone, Betahistine mesylate.
22. Antihypertensive agents
    Dimethylaminoethyl reserpinate hydrochloride, Rescinnamine, Methyldopa, Prazosin hydrochloride, Clonidine hydrochloride, Butofrazine.
23. Sympathomimetic agents
    Dihydroergotamine mesylate, Isoproterenol hydrochloride, Etilefrine hydrochloride
24. Expectorants
    Bromhexine hydrochloride, Carbocisteine, Ethylcysteine hydrochloride, Methylcysteine hydrochloride.
25. Oral agents for the treatment of diabetes
    Glibenclamide, Tolbutamide, Glymidine Sodium.
26. Agents for circulatory organs
    Ubidecarenone, ATP-2Na.
27. Iron agents
    Ferrous sulfate, Dry iron sulfate
28. Vitamins
    Vitamin $B_1$, Vitamin $B_2$, Vitamin $B_6$, Vitamin $B_{12}$, Vitamin C, folic acid.
29. Agents for the treatment of pollakiuria
    Flavoxate hydrochloride, Oxybutynin hydrochloride, Terodiline hydrochloride, 4-diethylamino-1,1-dimethyl-2-butynyl (±)-α-cyclohexyl-α-phenylglycolate hydrochloride monohydrate.

FUNCTION OF THE INVENTION

It is confirmed that, where the preparation in accordance with the present invention is put in an aqueous medium (for example, gastric juice, artificial gastric juice), the rapid release portion is firstly released immediately and a hydrated gel layer is then formed at the interface between the medium and the sustained release portion, whereby a drug in the preparation is slowly released and invasion of the liquid into the inside of the preparation is prevented to maintain suspension over a long period of time.

Also in this case, in the preparation in accordance with the present invention in which the substance in accordance with the present invention which can control release of the drug, the phenomenon of excessive prevention which might be caused, for example, where the drug is contained in an extremely small amount, or where a sparingly soluble drug is used.

That is, by adding the substance in accordance with the present invention which controls release of the drug, the preparation exhibits the effects of accelerating permeation of the liquid into the inside of the preparation, assisting a rate of hydration and accelerating separation of the hydrated gel layer.

The effects can be controlled by kind and addition amount of the substance which controls release of the drug in accordance with the present invention, whereby the release rate of various drugs can be optionally controlled.

When peristaltic motion is caused in stomach, a preparation having a poor strength is destroyed to lose the function as a sustained release preparation. In the preparation of the present invention, there is no chance to cause such.

In the preparation in accordance with the present invention, it is confirmed that the sustained release portion is not collapsed for 3 to 6 hours or longer when a disc is put on a collapse tester defined in the Japanese Pharmacopeia and a collapse test is carried out, and during the test, a definite amount of the drug component is released.

BEST MODE FOR PRACTICING THE INVENTION

Hereinafter the present invention is described in detail, with reference to the examples for producing the preparations in accordance with the present invention and test examples thereof.

EXAMPLE 1

As a rapid release portion, 3 g of riboflavin and 22 g of corn starch are taken and uniformly mixed in a mortar and 25 mg each of the mixture was packed in a capsule having a size of No. 2. Then, 3 g of riboflavin, 16 g of stearic acid, 16 g of hydroxypropyl cellulose H type and 48 g of microcrystalline cellulose are taken as a sustained release portion in a mortar and mixed uniformly. Thereafter 195 mg each of the mixture is packed in the capsule in which the rapid release portion has already been packed.

The capsule is heated for 10 minutes in an electric thermostat set at 70° C., then taken out and allowed to cool to obtain the capsule containing 3 mg of riboflavin in the rapid release portion and 7 mg of riboflavin in the sustained release portion.

EXAMPLE 2

As a rapid release portion, 15 g of diphenidol hydrochloride and 50 g of corn starch are taken and uniformly mixed in a mortar and 65 mg each of the mixture was packed in a capsule having a size of No. 2. Then, 15 g of diphenidol hydrochloride, 42 g of stearic acid, 42 g of polyacrylic acid and 36 g of microcrystalline cellulose are taken as a sustained release portion in a mortar and mixed uniformly. Thereafter 155 mg each of the mixture is packed in the capsule in which the rapid release portion has already been packed. Thereafter the capsule is subjected to a heat treatment in the same manner as in Example 1. Thus, the capsule containing 15 mg of diphenidol hydrochloride in the rapid release portion and 35 mg of diphenidol hydrochloride in the sustained release portion.

EXAMPLE 3

As a rapid release portion, 30 g of riboflavin, 110 g of lactose and 110 g of corn starch are taken in a fluidizing bed granulation drier (STREA, manufactured by Fuji Industry Co., Ltd.) and 80 ml of an aqueous solution containing polyvinyl alcohol was sprayed over the mixture for granulation. Then 25 mg each of the granules was packed in a capsule having a size of No. 2. Furthermore, 15 g of riboflavin, 160 g of stearyl alcohol, 160 g of alpha amylopectin and 80 g of hydroxypropyl cellulose having a low substitution degree are taken as a sustained release portion in a fluidizing bed granulation drier followed by spraying 250 ml of purified water for granulation. After 195 mg each of the granules is packed in the capsule in which the rapid release portion has already been packed. Thereafter the capsule is subjected to a heat treatment in the same manner as in Example 1 to give the capsule in which riboflavin is contained in 3 mg in the rapid release portion and 7 mg in the sustained release portion.

EXAMPLE 4

As a rapid release portion, 30 g of oxybutynin hydrochloride, 110 g of lactose and 200 g of corn starch are taken in a fluidizing bed granulation drier and 120 ml of an aqueous solution containing polyvinyl alcohol was sprayed over the mixture for granulation. Furthermore, 14 g of oxybutynin hydrochloride, 76.5 g of stearic acid, 76.5 g of hydroxypropyl cellulose H type and 153 g of microcrystalline cellulose are taken as a sustained release portion in a fluidizing bed granulation drier followed by spraying 150 ml of purified water for granulation. After 40 mg the rapid release portion and 160 mg of the sustained release portion were packed in a No. 2 capsule with a capsule packing machine of Model GKF-600 (manufactured by Hefriger) which has been modified to allow these granules to pack in a bilayer, the capsule is subjected to a heat treatment in the same manner as in Example 1 to give the capsule containing 3 mg of oxybutynin hydrochloride in the rapid release portion and 7 mg of oxybutynin hydrochloride in the sustained release portion.

EXAMPLE 5

As a rapid release portion, 50 g of oxybutynin hydrochloride, 150 g of lactose and 200 g of corn starch are taken in a fluidizing bed granulation drier and 200 ml of an aqueous solution containing polyvinyl alcohol was sprayed over the mixture for granulation. Furthermore, 10 g of oxybutynin hydrochloride, 77.5 g of stearic acid, 77.5 g of hydroxypropyl cellulose H type and 155 g of microcrystalline cellulose are taken as a sustained release portion in a fluidizing bed granulation drier followed by spraying 155 ml of purified water for granulation. After 40 mg the rapid release portion and 160 mg of the sustained release portion were packed in a No. 2 capsule with a capsule packing machine of Model GKF-600, the capsule is subjected to a heat treatment in the same manner as in Example 1 to give the capsule containing 5 mg of oxybutynin hydrochloride in the rapid release portion and 5 mg of oxybutynin hydrochloride in the sustained release portion.

EXAMPLE 6

As a rapid release portion, 10 g of oxybutynin hydrochloride, 195 g of lactose and 195 g of corn starch are taken in a fluidizing bed granulation drier and 150 ml of an aqueous solution containing polyvinyl alcohol was sprayed over the mixture for granulation. Furthermore, 18 g of oxybutynin hydrochloride, 190 g of hardened castor oil, 82 g of methyl cellulose (METOROSE SM-25, SHIN-ETSU KAGAKU Co.) and 30 g of microcrystalline cellulose are taken as a sustained release portion in a fluidizing bed granulation drier followed by spraying 200 ml of purified water for granulation. After 40 mg the rapid release portion and 160 mg of the sustained release portion were packed in a No. 2 capsule, the capsule is heated in an electric thermostat set at 100° C. for 10 minutes, then taken out and allowed to cool to room temperature to give the capsule containing 1 mg of oxybutynin hydrochloride in the rapid release portion and 9 mg of the same drug in the sustained release portion.

EXAMPLE 7

As a rapid release portion, 32 g of methyl 2,6-dimethyl -4-(2-nitrophenyl)-5-(2-oxo-1,3,2-dioxaphospholynan -2-yl)-1,4-dihydropyridine-3-carboxylate, 184 g of lactose and 184 g of corn starch are taken in a fluidizing bed granulation drier and 130 ml of an aqueous solution containing polyvinyl alcohol was sprayed over the mixture for granulation. Furthermore, 12.8 g of methyl 2,6-dimethyl -4-(2-nitrophenyl)-5-(2-oxo-1,3,2-dioxaphospholynan -2-yl)-1,4-dihydropyridine-3-carboxylate, 147.6 g of stearic acid, 147.6 g of hydroxypropyl cellulose H type and 52 g of microcrystalline cellulose are taken as a sustained release portion in a fluidizing bed granulation drier followed by spraying 150 ml of purified water for granulation. After 20 mg the rapid release portion and 180 mg of the sustained release portion were packed in a No. 2 capsule with a capsule packing machine of Model GKF-600, the capsule is subjected to a heat treatment in the same manner as in Example 1 to give the capsule containing 1.6 mg of methyl -2,6-dimethyl-4-(2-nitrophenyl)-5-(2-oxo-1,3,2-dioxaphospholynan -2-yl)-1,4-dihydropyridine-3-carboxylate in the rapid release portion and 6.4 mg of methyl 2,6-dimethyl -4-(2-nitrophenyl)-5-(2-oxo-1,3,2-dioxaphospholynan-2-yl) -1,4-dihydropyridine-3-carboxylate in the sustained release portion.

EXAMPLE 8

As a rapid release portion, 20 g of 4-diethyl -aminodiethyl-2-butynyl (±)-α-cyclohexyl-α-phenylglycolate hydrochloride monohydrate, 190 g of lactose and 190 g of corn starch are taken in a fluidizing bed granulation drier and 1530 ml of an aqueous solution containing polyvinyl alcohol was sprayed over the mixture for granulation. Furthermore, 24 g of 4-diethylamino-diethyl-2-butynyl (±)-α-cyclohexyl-α-phenylglycolate hydrochloride monohydrate, 164.5 g of stearic acid, 164.5 g of hydroxypropyl cellulose H type and 37 g of microcrystalline cellulose are taken as a sustained release portion in a fluidizing bed granulation drier followed by spraying 200 ml of purified water for granulation. After 40 mg the rapid release portion and 130 mg of the sustained release portion were packed in a No. 3 capsule with a capsule packing machine of Model GKF-600, the capsule is subjected to a heat treatment in the same manner as in Example 1 to give the capsule containing 2 mg of 4-diethylamino -diethyl-2-butynyl (±)-α-cyclohexyl-αphenylglycolate hydrochloride monohydrate in the rapid release portion and 8 mg of 4-diethylamino-diethyl-2-butynyl (±)-α-cyclohexyl -α-phenylglycolate hydrochloride monohydrate in the sustained release portion.

EXAMPLE 9

As a rapid release portion, 150 g of Cefalexin and 100 g of corn starch are taken in a V-shaped mixer (manufactured by FUJI Industry Co., Model FM-V-10) and mixed for 10 minutes. In a No. 0 capsule 125 mg each of the mixture is packed. Furthermore, 175 g of Cefalexin, 90 g of stearic acid, 45 g of hydroxypropylmethyl cellulose (METOROSE 90SH, SHIN-ETSU KAGAKU Co.) and 15 g of hydroxypropyl cellulose having a low degree substitution are taken as a sustained release portion in a V-shaped mixer and mixed for 10 minutes. Thereafter 325 mg each of the mixture is packed in the capsule in which the rapid release portion has previously been packed. The capsule is heated in an electric thermostat set at 100° C. for 10 minutes, then taken out and allowed to cool to room temperature to give the capsule containing 75 mg of Cefalexin in the rapid release portion and 175 mg of the same drug in the sustained release portion.

EXAMPLE 10

As a rapid release portion, 60 g of Nifedipine, 170 g of lactose and 170 g of corn starch are taken in a fluidizing bed granulation drier and 130 ml of an aqueous solution containing polyvinyl alcohol was sprayed over the mixture for granulation. Furthermore, 24 g of Nifedipine, 118 g of hardened castor oil, 118 g of hydroxypropyl cellulose L type and 60 g of microcrystalline cellulose are taken as a sustained release portion in a fluidizing bed granulation drier followed by spraying 150 ml of purified water for granulation. After 20 mg the rapid release portion and 160 mg of the sustained release portion were packed in a No. 3 capsule, the capsule is subjected to a heat treatment in the same manner as in Example 6 to give the capsule containing 3 mg of Nifedipine in the rapid release portion and 12 mg of the same drug in the sustained release portion.

EXAMPLE 11

As a rapid release portion, 54 g of chlorpheniramine maleate, 160.5 g of lactose and 160.5 g of corn starch are taken in a fluidizing bed granulation drier and 100 ml of an aqueous solution containing polyvinyl alcohol was sprayed over the mixture for granulation. Furthermore, 16.8 g of chlorpheniramine maleate, 104.8 g of stearic acid, 156.8 g of polyacrylic acid and 112 g of microcrystalline cellulose are taken as a sustained release portion in a fluidizing bed granulation drier followed by spraying 100 ml of purified water for granulation. After 25 mg the rapid release portion and 195 mg of the sustained release portion were packed in a No. 2 capsule with a capsule packing machine of Model GKF-600, the capsule is subjected to a heat treatment in the same manner as in Example 1 to give the capsule containing 3.6 mg of chlorpheniramine maleate in the rapid release portion and 8.4 mg of chlorpheniramine maleate in the sustained release portion.

The excellent properties of the preparation in accordance with the present invention can be confirmed by the following experiments.

Experiment 1. Dissolution Test

According to the second method (paddle method) in dissolution test defined in the Japanese Pharmacopeia, Sample is sunk in First Solution with a sinker. Stirring is performed at a paddle rotary number of 100 rpm, whereby a dissolution rate of each ingredient is determined. Oxybutynin hydrochloride and 4-diethylamino-1,1-dimethyl-2-butynyl (±)-α-cyclohexyl-α-phenyl glycolate hydrochloride monohydrate are subjected to sampling every time and determined by high performance liquid chromatography. In the case of riboflavin, absorbance is determined at 445 nm. The results are shown in FIGS. 1 through 3.

Experiment 2. Determination of buoyancy

Utilizing a micro loading converter (UT-100GR: manufactured by Shinkoh Minebea), an attachment for fixing a capsule is mounted to the converter and buoyancy of the capsule is determined every time during the dissolution test. The results are shown in FIG. 4.

The preparation of the present invention releases a drug slowly and maintains release of the drug controlled to an optional rate, after the preparation is put in water and its rapid release portion is rapidly released. It is evident that by such, the form having both rapid release property and sustained released property is obtained.

The foregoing results reveal that where the preparation of the present invention is orally administered, the preparation enables to increase the concentration of a drug to its therapeutic level in a short period of time after administration and then its sustained release portion is suspended in gastric juice or in the upper part of the gastric content, has a strength against gastric stirring motion and peristaltic motion so as not to be destroyed and slowly releases the drug in the stomach.

INDUSTRIAL APPLICABILITY

Figure 1:
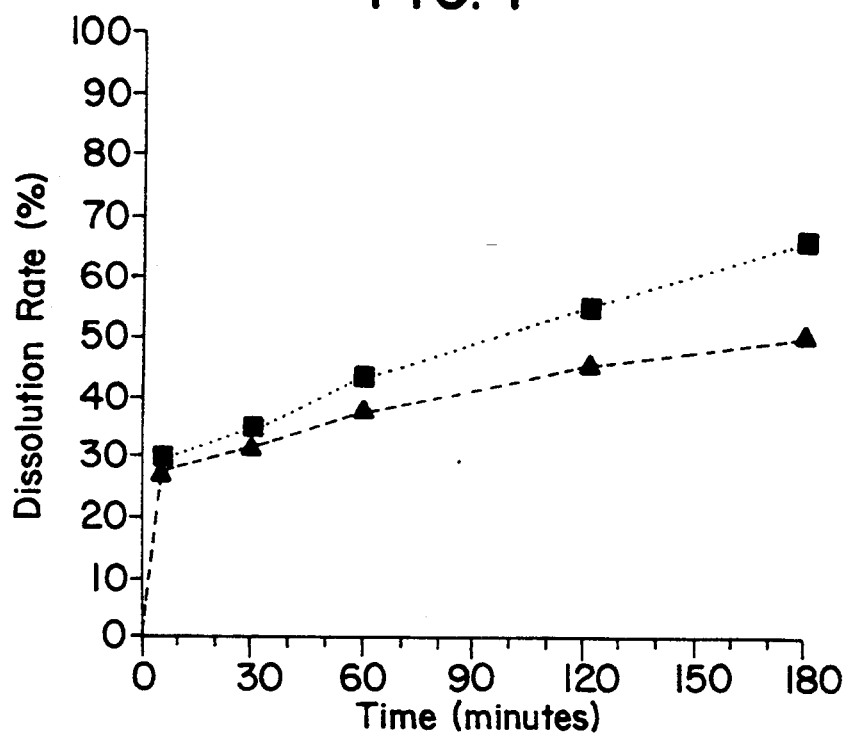
In FIG. 1, black square and black triangle indicate the preparation of Example 1 and the preparation of Example 3, respectively, and each represents a dissolution rate of riboflavin, wherein the abscissa shows time (minute) and the ordinate shows dissolution rate (%), respectively.
Figure 2:
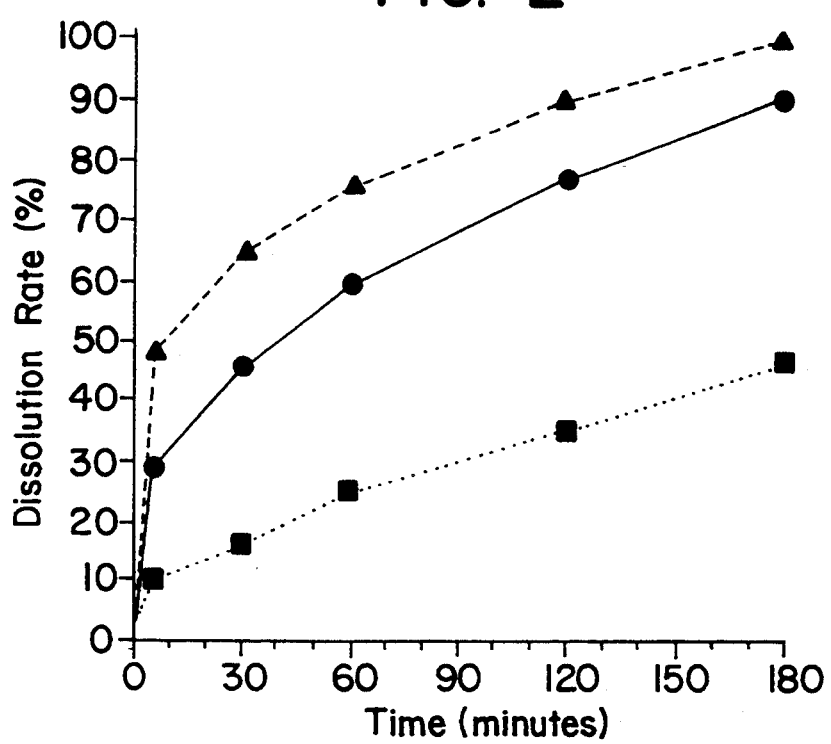
In FIG. 2, black circle, black triangle and black square indicate the preparation of Example 4, the preparation of Example 5 and the preparation of Example 6, respectively, and each represents a dissolution rate of Oxybutynin hydrochloride, wherein the abscissa shows time (minute) and the ordinate shows dissolution rate (%), respectively.
Figure 3:
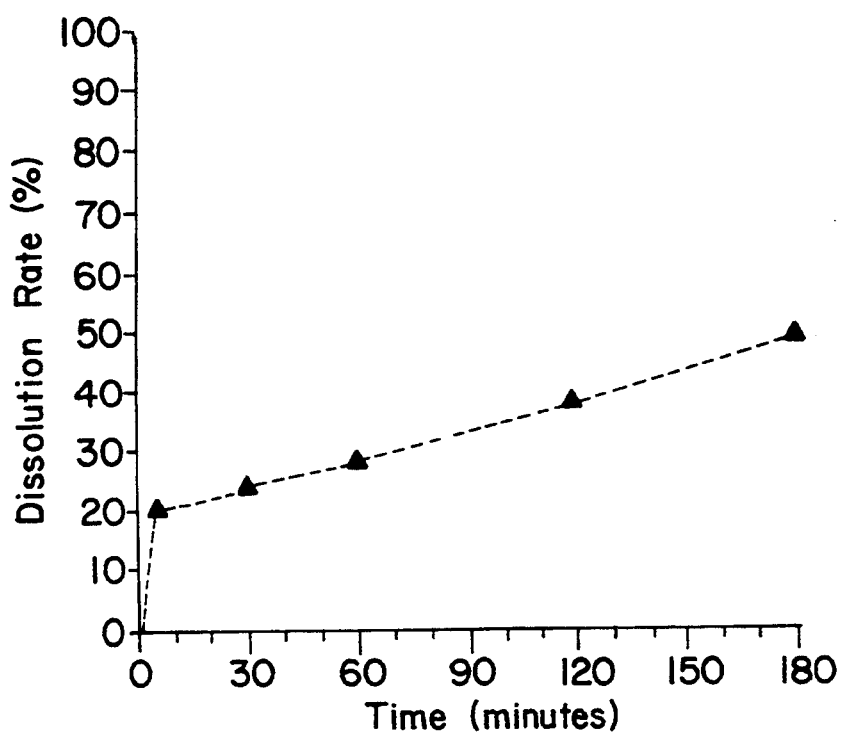
FIG. 3 shows the preparation of Example 8 and represents a dissolution rate of 4-diethylamino-1,1-dimethyl-2-butynyl (±)-α-cyclohexyl-α-phenylglycolate hydrochloride monohydrate, in which the abscissa shows time (minute) and the ordinate shows dissolution rate (%), respectively.
Figure 4:
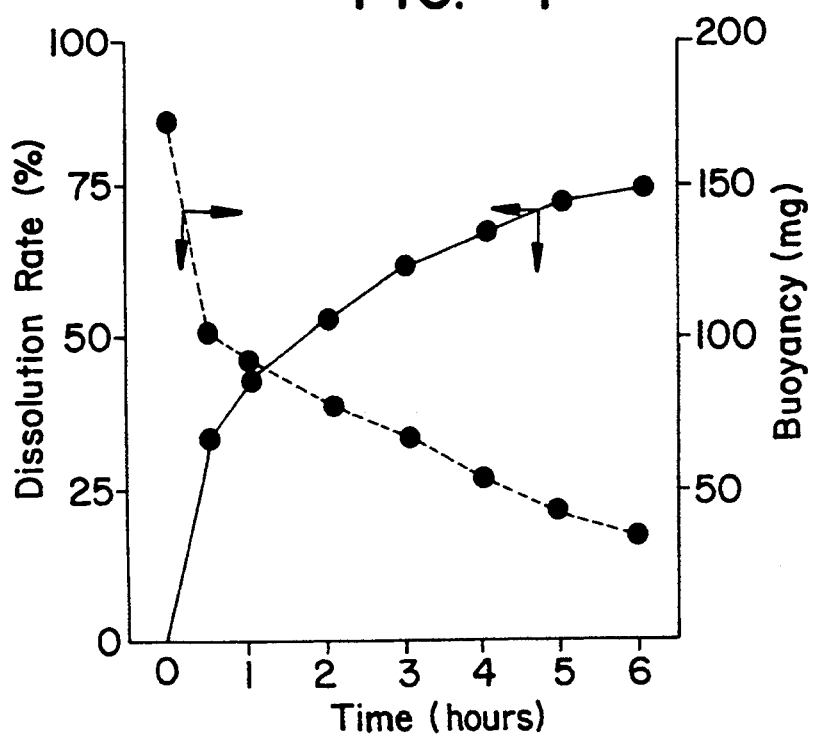
FIG. 4 shows a dissolution rate of the riboflavin preparation obtained in Example 1 and buoyancy at that time. Solid line obtained by connecting black circles and dashed line line obtained by connecting black circles show dissolution curve and change in buoyancy, respectively. The abscissa, the left ordinate and the right ordinate show time (hour), dissolution rate (%) and buoyancy (mg), respectively.

As described above, the present invention has the following excellent technical effects and is useful as a device for medical drugs.

(1) The preparation in accordance with the present invention shows, when put in an aqueous medium, rapid disintegration in a part of the preparation which is a rapid release portion and hence, can maintain a therapeutic level of a drug in a short period of time after administration.

(2) The preparation in accordance with the present invention assures suspendability in an aqueous medium and therefore, maintains its suspended state in stomach to exhibit reliable sustained release.

(3) The preparation in accordance with the present invention has an appropriate strength so that the preparation is not disintegrated rapidly by peristaltic motion in stomach.

(4) The preparation in accordance with the present invention can provide an optional release rate so that the preparation can be designed to cope with the property of a drug.

(5) The preparation in accordance with the present invention has reproducibility pertinent to a release rate in an aqueous medium so that the preparation can maintain release of an effective drug in a constant amount during being suspended in stomach.

We claim:

1. A gastric preparation comprising a predetermined effective amount of a drug, said preparation comprising a rapid release portion from which said drug is rapidly released and a sustained release portion from which said drug is gradually released, the two portions being released simultaneously to form a layer, wherein said sustained release portion comprises:

(a) a substance capable of producing a gel in water,
  (b) an oil or fat which is solid under ambient temperature conditions,
  (c) a drug, and
  (d) a hydrophilic or swellable substance for controlling release of the drug; and the specific gravity of the preparation being not more than 1.

2. A gastric preparation comprising a predetermined effective amount of a drug, said preparation comprising a rapid release portion from which said drug is rapidly released and a sustained release portion from which said drug is gradually released, the two portions being released simultaneously to form a layer, wherein said rapid release portion comprises a drug or a drug and an excipient, wherein said sustained release portion comprises:

(a) a substance capable of producing a gel in water, wherein said substance is selected from the group consisting of carboxymethyl cellulose, carboxyethyl cellulose, carboxypropyl cellulose, an alkali salt of carboxymethyl cellulose, an alkali salt of carboxyethyl cellulose, an alkali salt of carboxypropyl cellulose, methyl cellulose, hydroxypropyl cellulose, hydroxyethyl cellulose, alpha starch, alpha amylostarch, gelatinized starch, carboxymethylated starch, carboxyethylated starch, phosphated starch, acid-treated starch, oxidized starch, dialdehyde starch, soluble starch, thin-boiling starch, dextrin, dextran, dextran sulfate, carboxymethyl dextran, polysaccharides, rubbers, polypeptides, proteins, polyacrylic acid, polymethacrylic acid, an alkali salt of polymethacrylic acid, a copolymer of polyacrylic acid, polymethacrylic acid, polyvinylpyrrolidone and polyvinyl alcohol, (b) an oil or fat which is solid under ambient temperature conditions, wherein said oil or fat is selected from the group consisting of higher fatty acids; esters of lauric acid, trideconoic acid, myristic acid, pentadecanoic acid, palmitic acid, margaric acid, steric acid, nonadecanoic acid, arrachic acid, behenic acid, lignoseric acid, serotic acid and montanic acid; glycerides of saturated fatty acids obtained from animal and plant; a mixture thereof with hardened oil and fat of the glycerides derived from the animal and plant; glycerides of unsaturated fatty acids; higher alcohols; cholesteryl palmitate; and palmitate of plant sterol, (c) a drug, and
  (d) a hydrophilic or swellable substance for controlling release of the drug wherein said substance
  (d) of said sustained release portion is selected from the group consisting of fine crystalline cellulose, hydroxypropyl cellulose of low substitution degree, corn starch, mannitol, refined sugar and lactose; and the specific gravity of the preparation being not more than 1.

3. The gastric preparation according to claim 1 in the form of a capsule, wherein said preparation comprises said rapid release portion and said sustained release portion within the same capsule.

4. The gastric preparation according to claim 1 wherein said substance (a) of said sustained release portion is wherein said rapid release portion comprises 5% to 60% of said preparation, and said sustained release portion comprises 40% to 95% of said preparation.

5. The gastric preparation according to claim 1 wherein said rapid release portion comprises 10% to 40% of said preparation, and said sustained release portion comprises 60% to 90% of said preparation.

6. The preparation according to claim 1, wherein each of said portions is in the form of contacting layers.

7. The gastric preparation according to claim 1, selected from the group consisting of carboxymethyl cellulose, carboxyethyl cellulose, carboxypropyl cellulose, an alkali salt of carboxymethyl cellulose, an alkali salt of carboxyethyl cellulose, an alkali salt of carboxypropyl cellulose, methyl cellulose, hydroxypropyl cellulose, hydroxyethyl cellulose, alpha starch, alpha amylostarch, gelatinized starch, carboxymethylated starch, carboxyethylated starch, phosphated starch, acid-treated starch, oxidized starch, dialdehyde starch, soluble starch, thin-boiling starch, dextrin, dextran, dextran sulfate, carboxymethyl dextran, polysaccharides, rubbers, polypeptides, proteins, polyacrylic acid, polymethacrylic acid, an alkali salt of polymethacrylic acid, a copolymer of polyacrylic acid, polymethacrylic acid, polyvinylpyrrolidone and polyvinyl alcohol.

8. The gastric preparation according to claim 1 wherein said oil of fat (b) of said sustained release portion is selected from the group consisting of higher fatty acids; esters of lauric acid, trideconoic acid, myristic acid, pentadecanoic acid, palmitic acid, margaric acid, stearic acid, nonadecanoic acid, arachic acid, behenic acid, lignoseric acid, serotic acid and montanic acid; glycerides of saturated fatty acids obtained from animal and plant; a mixture thereof with hardened oil and fat of the glycerides derived from the animal and plant; glycerides of unsaturated fatty acids; higher alcohols; cholesteryl palmitate; and palmitate of plant sterol.

9. The gastric preparation according to claim 1 wherein said substance (d) of said sustained release portion is selected from the group consisting of fine crystalline cellulose, hydroxypropyl cellulose of low substitution degree, corn starch, mannitol, refined sugar and lactose.

10. A method of making the gastric preparation according to claim 1, wherein said rapid release portion is placed into a capsule, said sustained release portion is placed into a capsule, each portion forms a layer within said capsule, and the preparation is heated then allowed to cool.

* * * * *